(12) United States Patent
Woo et al.

(10) Patent No.: US 8,461,089 B2
(45) Date of Patent: Jun. 11, 2013

(54) DISHWASHING DETERGENT COMPOSITION HAVING A MALODOR CONTROL COMPONENT AND METHODS OF CLEANING DISHWARE

(75) Inventors: Ricky Ah-Man Woo, Hamilton, OH (US); Steven Anthony Horenziak, Cincinnati, OH (US); Rhonda Jean Jackson, Cincinnati, OH (US); Zaiyou Liu, West Chester, OH (US); Michael-Vincent Nario Malanyaon, Indian Springs, OH (US); Jason John Olchovy, West Chester, OH (US); Christine Marie Readnour, Fort Mitchell, KY (US)

(73) Assignee: The Procter & Gamble Company, Cincinnati, OH (US)

( * ) Notice: Subject to any disclaimer, the term of this patent is extended or adjusted under 35 U.S.C. 154(b) by 165 days.

(21) Appl. No.: 12/969,639

(22) Filed: Dec. 16, 2010

(65) Prior Publication Data

US 2011/0152157 A1 Jun. 23, 2011

Related U.S. Application Data

(60) Provisional application No. 61/287,348, filed on Dec. 17, 2009, provisional application No. 61/287,369, filed on Dec. 17, 2009, provisional application No. 61/287,383, filed on Dec. 17, 2009.

(51) Int. Cl.
*C11D 1/00* (2006.01)
*C11D 3/34* (2006.01)
*C11D 3/50* (2006.01)

(52) U.S. Cl.
USPC ........... 510/101; 510/220; 510/221; 510/223; 510/224; 510/229; 510/235; 510/237; 510/480; 510/488; 510/492; 510/503; 510/505

(58) Field of Classification Search
USPC ................ 510/101, 220, 221, 223, 224, 229, 510/235, 237, 480, 503, 505; 134/25.2
See application file for complete search history.

(56) References Cited

U.S. PATENT DOCUMENTS

| | | | |
|---|---|---|---|
| 5,942,217 | A | 8/1999 | Woo et al. |
| 5,955,093 | A | 9/1999 | Woo et al. |
| 6,033,679 | A | 3/2000 | Woo et al. |
| 6,306,812 | B1 | 10/2001 | Perkins et al. |
| 6,362,147 | B1 | 3/2002 | Castro et al. |
| 7,135,449 | B2 | 11/2006 | Li et al. |
| 7,169,741 | B2 | 1/2007 | Barry et al. |
| 7,199,093 | B2 | 4/2007 | Li et al. |
| 7,393,521 | B2 | 7/2008 | Hruza |
| 7,425,526 | B2 | 9/2008 | Li et al. |
| 2004/0018955 | A1 | 1/2004 | Wevers et al. |
| 2007/0135319 | A1* | 6/2007 | Wei et al. ................. 510/101 |
| 2007/0294328 | A1 | 12/2007 | Schneiderman et al. |
| 2008/0032910 | A1 | 2/2008 | Smets et al. |
| 2008/0194454 | A1 | 8/2008 | Morgan et al. |
| 2008/0200359 | A1 | 8/2008 | Smets et al. |

FOREIGN PATENT DOCUMENTS

| | | |
|---|---|---|
| EP | 1111034 A1 | 6/2001 |
| EP | 2008637 A1 | 12/2008 |
| WO | WO-0123516 A1 | 4/2001 |

OTHER PUBLICATIONS

International Search Report dated Dec. 16, 2010 containing 152 pages.

* cited by examiner

*Primary Examiner* — Gregory Delcotto
(74) *Attorney, Agent, or Firm* — John T. Dipre; Amy I. Ahn-Roll

(57) ABSTRACT

A dishwashing detergent composition comprising a malodor control component, and methods of cleaning dishware are provided. In some embodiments, the dishwashing detergent composition comprises at least one volatile aldehyde and an acid catalyst.

10 Claims, 1 Drawing Sheet

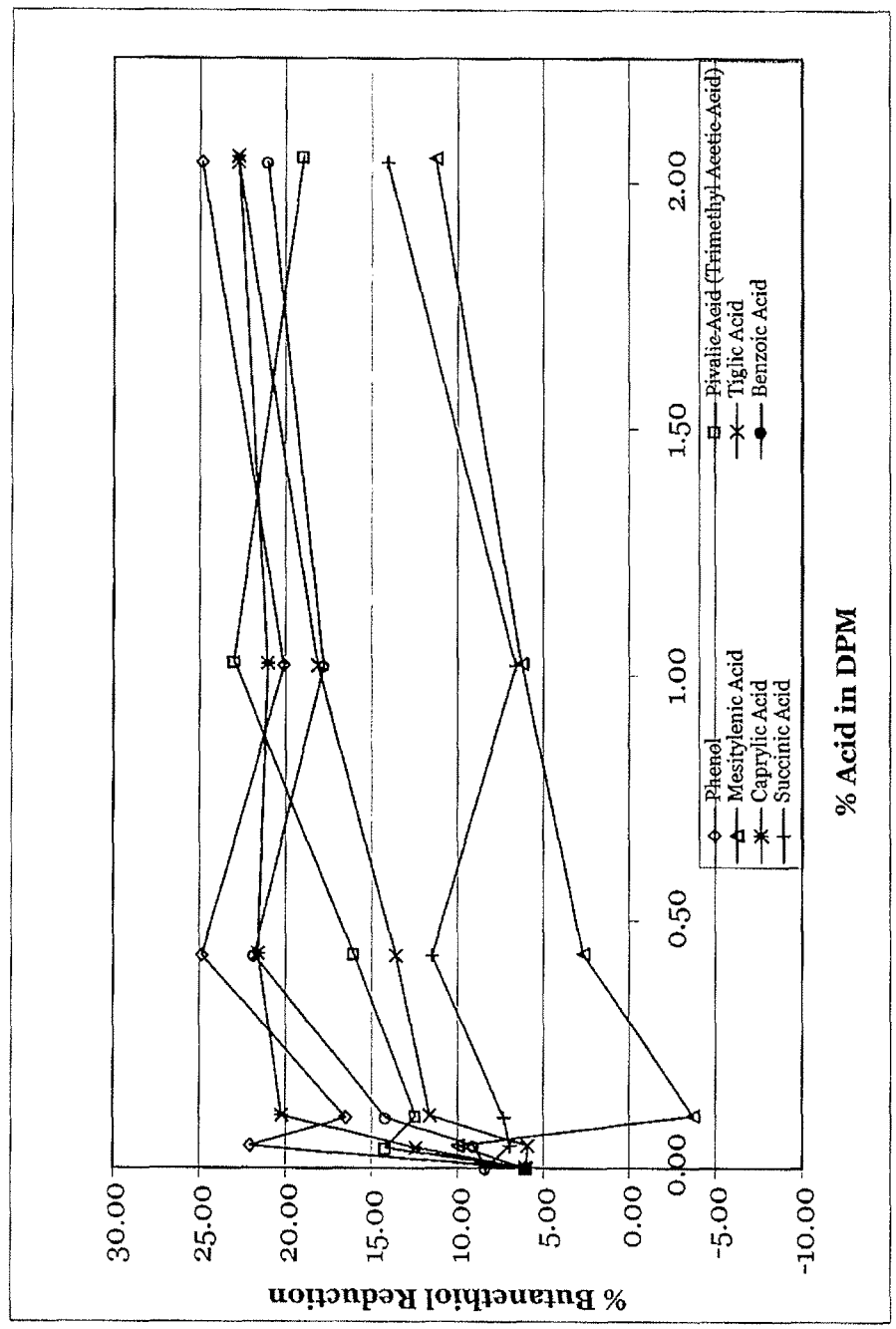

DISHWASHING DETERGENT COMPOSITION HAVING A MALODOR CONTROL COMPONENT AND METHODS OF CLEANING DISHWARE

CROSS REFERENCE TO RELATED APPLICATIONS

This application claims the benefit of U.S. Provisional Application No. 61/287,348, filed Dec. 17, 2009 and U.S. Provisional Application No. 61/287,369, filed Dec. 17, 2009 and U.S. Provisional No. 61/287,383, filed Dec. 17, 2009.

FIELD OF THE INVENTION

The present invention relates to dishwashing detergent compositions having a malodor control component, and methods of cleaning dishware.

BACKGROUND OF THE INVENTION

Scented dishwashing detergent products for cleaning dishware are known. Typically, dishwashing detergent manufacturers develop perfume technology that provides a pleasant scent and masks malodors associated with soiled dishware.

However, not all odors are effectively controlled by products on the market as amine-based malodors such as fish malodors, and sulfur-based malodors such as garlic and onion are difficult to combat. Further, the time required for a product to noticeably combat malodors may create consumer doubt as to a product's efficacy on malodors. For example, the consumer may finish washing a dish and leave the area before the product begins to noticeably reduce the malodor.

The difficulty in overcoming a broad range of malodors has spawned a diverse assortment of products to neutralize, mask, or contain the malodors. There remains a need for a dishwashing detergent composition that cleans dishware and is effective on a broad range of malodors, including amine-based and sulfur-based malodors, while not overpowering malodors with an overwhelming perfume.

SUMMARY OF THE INVENTION

In one embodiment, there is provided a dishwashing detergent composition comprising: (a) from about 0.1% to about 20% by weight of the total composition of a chelant; (b) from about 5% to about 80% by weight of the total composition of a surfactant selected from the group consisting of anionic, nonionic, cationic, amphoteric, zwitterionic, semi-polar nonionic surfactants and mixtures thereof; and (c) a malodor control component comprising an effective amount of two or more volatile aldehydes for neutralizing a malodor, wherein said two or more volatile aldehydes are selected from the group consisting of 2-ethoxy benzylaldehyde, 2-isopropyl-5-methyl-2-hexenal, 5-methyl furfural, 5-methyl-thiophene-carboxaldehyde, adoxal, p-anisaldehyde, benzylaldehyde, bourgenal, cinnamic aldehyde, cymal, decyl aldehyde, floral super, florhydral, helional, lauric aldehyde, ligustral, lyral, melonal, o-anisaldehyde, pino acetaldehyde, P.T. bucinal, thiophene carboxaldehyde, trans-4-decenal, trans trans 2,4-nonadienal, undecyl aldehyde, and mixtures thereof.

In another embodiment, there is provided a dishwashing detergent composition comprising: (a) a chelant; (b) a surfactant selected from the group consisting of anionic, nonionic, cationic, amphoteric, zwitterionic, semi-polar nonionic surfactants, and mixtures thereof; and (c) a malodor control component comprising: (i) at least one volatile aldehyde; and (ii) an acid catalyst having a vapor pressure of about 0.01 to about 13 at 25° C.; and (b) about 1% to about 5%, by weight of said composition, of a low molecular weight monohydric alcohol.

In another embodiment, there is provided a method of cleaning a dishware comprising the steps of: applying a composition according to claim 1 on said dishware; and rinsing said composition off of said dishware.

BRIEF DESCRIPTION OF THE DRAWINGS

FIG. 1 is a graph showing butanethiol reduction by thiophene carboxaldehyde in combination with various acid catalysts.

DETAILED DESCRIPTION OF THE INVENTION

The present invention relates to a dishwashing detergent composition that surprisingly provides excellent grease cleaning combined with superior shine and malodor control; and methods of cleaning dishware.

"Cleaning" means applying to a surface for the purpose of cleaning, and/or disinfecting.

"Dishware" means a surface such as dishes, glasses, pots, pans, baking dishes and flatware made from ceramic, china, metal, glass, plastic (polyethylene, polypropylene, polystyrene, etc.) and wood.

"Dishwashing detergent composition" refers to those compositions that are employed in manual (i.e. hand) dishwashing. Such compositions are generally high sudsing or foaming in nature.

"Grease" means materials comprising at least in part (i.e., at least 0.5 wt % by weight of the grease) saturated and unsaturated fats and oils, alternatively oils and fats derived from animal sources such as beef and/or chicken.

"Malodor" refers to compounds generally offensive or unpleasant to most people, such as the complex odors associated with bowel movements.

"Neutralize" or "neutralization" refers to the ability of a compound or product to reduce or eliminate malodorous compounds. Odor neutralization may be partial, affecting only some of the malodorous compounds in a given context, or affecting only part of a malodorous compound. A malodorous compound may be neutralized by chemical reaction resulting in a new chemical entity, by sequestration, by chelation, by association, or by any other interaction rendering the malodorous compound less malodorous or non-malodorous. Odor neutralization may be distinguished from odor masking or odor blocking by a change in the malodorous compound, as opposed to a change in the ability to perceive the malodor without any corresponding change in the condition of the malodorous compound.

"Suds profile" means the amount of sudsing (high or low) and the persistence of sudsing (sustained sudsing) throughout the washing process resulting from the use of the liquid detergent composition of the present composition. As used herein "high sudsing" refers to liquid hand dishwashing detergent compositions which are both high sudsing (i.e. a level of sudsing considered acceptable to the consumer) and have sustained sudsing (i.e. a high level of sudsing maintained throughout the dishwashing operation). This is particularly important with respect to liquid dishwashing detergent compositions as the consumer uses high sudsing as an indicator of the performance of the detergent composition. Moreover, the consumer of a liquid dishwashing detergent composition also uses the sudsing profile as an indicator that the wash solution still contains active detergent ingredients. The consumer usually renews the wash solution when the sudsing subsides. Thus, a low sudsing liquid dishwashing detergent composition formulation will tend to be replaced by the consumer more frequently than is necessary because of the low sudsing level.

I. Dishwashing Detergent Composition

The dishwashing detergent composition generally contains from 30% to 95%, alternatively 40% to 80%, alternatively 50% to 75% of an aqueous liquid carrier, in which the other essential and optional compositions components are dissolved, dispersed or suspended.

A. Chelant

The composition of the present invention comprises a chelant at a level of from 0.1% to 20%, alternatively from 0.2% to 5%, alternatively from 0.2% to 3% by weight of total composition.

As commonly understood in the detergent field, chelation herein means the binding or complexation of a bi- or multidentate ligand. These ligands, which are often organic compounds, are called chelants, chelators, chelating agents, and/or sequestering agent. Chelating agents form multiple bonds with a single metal ion. Chelants, are chemicals that form soluble, complex molecules with certain metal ions, inactivating the ions so that they cannot normally react with other elements or ions to produce precipitates or scale. The ligand forms a chelate complex with the substrate. The term is reserved for complexes in which the metal ion is bound to two or more atoms of the chelant. The chelants for use in the present invention are those having crystal growth inhibition properties, i.e. those that interact with the small calcium and magnesium carbonate particles preventing them from aggregating into hard scale deposit. The particles repel each other and remain suspended in the water or form loose aggregates which may settle. These loose aggregates are easily rinsed away and do not form a deposit.

Suitable chelating agents can be selected from the group consisting of amino carboxylates, amino phosphonates, polufanctionally-substituted aromatic chelating agents and mixtures thereof.

Suitable chelants for use herein are also the amino acids based chelants, alternatively glutamic-N,N-diacetic acid and derivatives and/or phosphonate based chelants, alternatively diethylenetriamine penta methylphosphonic acid.

Amino carboxylates include ethylenediaminetetra-acetates, N-hydroxyethylethylenediaminetriacetates, nitrilotriacetates, ethylenediamine tetrapro-prionates, triethylenetetraaminehexacetates, diethylenetriaminepentaacetates, and ethanoldi-glycines, alkali metal, ammonium, and substituted ammonium salts therein and mixtures therein. As well as MGDA (methyl-glycine-diacetic acid), and salts and derivatives thereof and GLDA (glutamic-N,N-diacetic acid) and salts and derivatives thereof. In one embodiment, the composition comprises GLDA (salts and derivatives thereof). In another embodiment, the composition comprises tetrasodium salt.

Other suitable chelants include amino acid based compound or a succinate based compound. The term "succinate based compound" and "succinic acid based compound" are used interchangeably herein. Other suitable chelants are described in U.S. Pat. No. 6,426,229. Particular suitable chelants include; for example, aspartic acid-N-monoacetic acid (ASMA), aspartic acid-N,N-diacetic acid (ASDA), aspartic acid-N-monopropionic acid (ASMP), iminosuccinic acid (IDS), Imino diacetic acid (IDA), N-(2-sulfomethyl) aspartic acid (SMAS), N-(2-sulfoethyl) aspartic acid (SEAS), N-(2-sulfomethyl) glutamic acid (SMGL), N-(2-sulfoethyl) glutamic acid (SEGL), N-methyliminodiacetic acid (MIDA), □-alanine-N,N-diacetic acid (□-ALDA), serine-N,N-diacetic acid (SEDA), isoserine-N,N-diacetic acid (ISDA), phenylalanine-N,N-diacetic acid (PHDA), anthranilic acid-N,N-diacetic acid (ANDA), sulfanilic acid-N, N-diacetic acid (SLDA), taurine-N, N-diacetic acid (TUDA) and sulfomethyl-N,N-diacetic acid (SMDA) and alkali metal salts or ammonium salts thereof. Also suitable is ethylenediamine disuccinate ("EDDS"), especially the [S,S] isomer as described in U.S. Pat. No. 4,704,233. Furthermore, Hydroxyethyleneiminodiacetic acid, Hydroxyiminodisuccinic acid, Hydroxyethylene diaminetriacetic acid are also suitable.

Other chelants include homopolymers and copolymers of polycarboxylic acids and their partially or completely neutralized salts, monomeric polycarboxylic acids and hydroxycarboxylic acids and their salts. Suitable salts of the above-mentioned compounds are the ammonium and/or alkali metal salts, i.e. the lithium, sodium, and potassium salts.

Suitable polycarboxylic acids are acyclic, alicyclic, heterocyclic and aromatic carboxylic acids, in which case they contain at least two carboxyl groups which are in each case separated from one another by, alternatively, no more than two carbon atoms. Polycarboxylates which comprise two carboxyl groups include, for example, water-soluble salts of, malonic acid, (ethyl enedioxy) diacetic acid, maleic acid, diglycolic acid, tartaric acid, tartronic acid and fumaric acid. Polycarboxylates which contain three carboxyl groups include, for example, water-soluble citrate. Correspondingly, a suitable hydroxycarboxylic acid is, for example, citric acid. Another suitable polycarboxylic acid is the homopolymer of acrylic acid. In one embodiment, the composition includes the polycarboxylates end capped with sulfonates.

Amino phosphonates are also suitable for use as chelating agents and include ethylenediaminetetrakis (methylenephosphonates) as DEQUEST. In one embodiment, the composition includes amino phosphonates that do not contain alkyl or alkenyl groups with more than about 6 carbon atoms.

Polyfunctionally-substituted aromatic chelating agents are also useful in the compositions herein such as described in U.S. Pat. No. 3,812,044. In one embodiment, the composition includes dihydroxydisulfobenzenes such as 1,2-dihydroxy-3, 5-disulfobenzene.

Further suitable polycarboxylates chelants for use herein include citric acid, lactic acid, acetic acid, succinic acid, formic acid; all alternatively in the form of a water-soluble salt. Other suitable polycarboxylates are oxodisuccinates, carboxymethyloxysuccinate and mixtures of tartrate monosuccinic and tartrate disuccinic acid such as described in U.S. Pat. No. 4,663,071.

B. Surfactants

The composition of the present invention may comprise a surfactant selected from anionic, nonionic, cationic, amphoteric, zwitterionic, semi-polar nonionic surfactants, and mixtures thereof. The surfactants of the composition will have an average branching of the alkyl chain(s) of more than 10%, alternatively more than 20%, alternatively more than 30%, alternatively more than 40%, by weight of the total surfactants.

The surfactants of the present invention will generally be present at a level of 5% to 80%, alternatively 10% to 60%, alternatively 12% to 45%, by weight of the total composition.

In one embodiment, the composition of the present invention will further comprise a nonionic surfactant at a weight ratio of total surfactant to nonionic surfactant of 2 to 10, alternatively of 2 to 7.5, alternatively of 2 to 6.

The surfactants described below can be used in their linear and/or branched version.

1. Nonionic Surfactants

It has been found that the addition of nonionic surfactants, alternatively of branched nonionic surfactants, will prevent efficiently the formation of crystalline films of the dish surface and will provide improved wetting and thereby providing superior shine.

Nonionic surfactants are present in a typical amount of from 2% to 40%, alternatively 3% to 30% by weight of the liquid detergent composition and alternatively from 3 to 20% by weight of the total composition. Suitable nonionic surfactants include the condensation products of aliphatic alcohols with from 1 to 25 moles of ethylene oxide. The alkyl chain of the aliphatic alcohol can either be straight or branched, primary or secondary, and generally contains from 8 to 22 carbon atoms. In one embodiment, the composition includes the condensation products of alcohols having an alkyl group containing from 8 to 18 carbon atoms, alternatively from 9 to 15 carbon atoms with from 2 to 18 moles, alternatively 2 to 15, alternatively 5-12 of ethylene oxide per mole of alcohol.

Also suitable are alkylpolyglycosides having the formula $R^2O(C_nH_{2n}O)_t(glycosyl)_x$ (formula (III)), wherein $R^2$ of formula (III) is selected from the group consisting of alkyl, alkyl-phenyl, hydroxyalkyl, hydroxyalkylphenyl, and mixtures thereof in which the alkyl groups contain from 10 to 18, alternatively from 12 to 14, carbon atoms; n of formula (III) is 2 or 3, alternatively 2; t of formula (III) is from 0 to 10, alternatively 0; and x of formula (III) is from 1.3 to 10, alternatively from 1.3 to 3, most alternatively from 1.3 to 2.7. The glycosyl is alternatively derived from glucose. Also suitable are alkyl glycerol ethers and sorbitan esters.

Also suitable are fatty acid amide surfactants having the formula (IV):

(IV)

wherein $R^6$ of formula (IV) is an alkyl group containing from 7 to 21, alternatively from 9 to 17, carbon atoms and each $R^7$ of formula (IV) is selected from the group consisting of hydrogen, $C_1$-$C_4$ alkyl, $C_1$-$C_4$ hydroxyalkyl, and —$(C_2H_4O)_x$H where x of formula (IV) varies from 1 to 3. Suitable amides are $C_8$-$C_{20}$ ammonia amides, monoethanolamides, diethanolamides, and isopropanolamides.

Suitable nonionic surfactants for use in the present invention are the condensation products of aliphatic alcohols with ethylene oxide, such as the mixture of nonyl (C9), decyl (C10) undecyl (C11) alcohol modified with on average 5 ethylene oxide (EO) units such as the commercially available Neodol 91-5 or the Neodol 91-8 that is modified with on average 8 EO units. Also suitable are the longer alkyl chains ethoxylated nonionics such as C12, C13 modified with 5 EO (Neodol 23-5). Neodol is a Shell tradename. Also suitable is the C12, C14 alkyl chain with 7 EO commercially available under the trade name Novel 1412-7 (Sasol) or the Lutensol A7N (BASF).

Suitable branched nonionic are the Guerbet C10 alcohol ethoxylates with 5 EO such as Ethylan 1005, Lutensol XP 50 and the Guerbet C10 alcohol alkoxylated nonionics (modified with EO and PO=propyleneoxyde) such as the commercially available Lutensol XL series (X150, XL70, . . . ). Other branching also include oxo branched nonionic surfactants such as the Lutensol ON 50 (5 EO) and Lutensol ON70 (7 EO). Other suitable branched nonionics are the ones derived from the isotridecyl alcohol and modified with ethyleneoxyde such as the Lutensol TO7 (7 EO) from BASF and the Marlipal O 13/70 (7 EO) from Sasol. Also suitable are the ethoxylated fatty alcohols originating from the Fisher & Troshp reaction comprising up to 50% branching (40% methyl (mono or bi) 10% cyclohexyl) such as those produced from the safol™ alcohols from Sasol; ethoxylated fatty alcohols originating from the oxo reaction wherein at least 50 weight % of the alcohol is C2 isomer (methyl to pentyl) such as those produced from the Isalchem™ alcohols or Lial™ alcohols from Sasol; the ethoxylated fatty alcohols originating from the modified oxo reaction wherein at least 15 weight % of the alcohol is C2 isomer (methyl to pentyl) such as those produced from the Neodol™ alcohols from Shell.

2. Amphoteric/Zwitterionic Surfactants

The amphoteric and zwitterionic surfactanta can be present at a level of from 0.01% to 20%, alternatively from 0.2% to 15%, alternatively 0.5% to 10%, by weight of the composition. The compositions of the present invention may further comprise an amine oxide and/or a betaine.

In one embodiment, the composition includes amine oxides are coco dimethyl amine oxide or coco amido propyl dimethyl amine oxide. Amine oxide may have a linear or mid-branched alkyl moiety. Typical linear amine oxides include water-soluble amine oxides containing one R1 $C_{8-18}$ alkyl moiety and 2 R2 and R3 moieties selected from the group consisting of $C_{1-3}$ alkyl groups and $C_{1-3}$ hydroxyalkyl groups. Alternatively, amine oxide is characterized by the formula R1–N(R2)(R3)→O wherein $R_1$ is a $C_{8-18}$ alkyl and $R_2$ and $R_3$ are selected from the group consisting of methyl, ethyl, propyl, isopropyl, 2-hydroxethyl, 2-hydroxypropyl and 3-hydroxypropyl. The linear amine oxide surfactants in particular may include linear $C_{10}$-$C_{18}$ alkyl dimethyl amine oxides and linear $C_8$-$C_{12}$ alkoxy ethyl dihydroxy ethyl amine oxides. Suitable amine oxides include linear $C_{10}$, linear $C_{10}$-$C_{12}$, and linear $C_{12}$-$C_{14}$ alkyl dimethyl amine oxides.

As used herein "mid-branched" means that the amine oxide has one alkyl moiety having $n_1$ carbon atoms with one alkyl branch on the alkyl moiety having $n_2$ carbon atoms. The alkyl branch is located on the α carbon from the nitrogen on the alkyl moiety. This type of branching for the amine oxide is also known in the art as an internal amine oxide. The total sum of $n_1$ and $n_2$ is from 10 to 24 carbon atoms, alternatively from 12 to 20, and alternatively from 10 to 16. The number of carbon atoms for the one alkyl moiety ($n_1$) should be approximately the same number of carbon atoms as the one alkyl branch ($n_2$) such that the one alkyl moiety and the one alkyl branch are symmetric. As used herein "symmetric" means that $|n_1-n_2|$ is less than or equal to 5, alternatively 4, alternatively from 0 to 4 carbon atoms in at least 50 wt %, alternatively at least 75 wt % to 100 wt % of the mid-branched amine oxides for use herein.

The amine oxide further comprises two moieties, independently selected from a $C_{1-3}$ alkyl, a $C_{1-3}$ hydroxyalkyl group, or a polyethylene oxide group containing an average of from about 1 to about 3 ethylene oxide groups. Alternatively, the two moieties are selected from a $C_{1-3}$ alkyl, alternatively both are selected as a $C_1$ alkyl.

Other suitable surfactants include betaines such alkyl betaines, alkylamidobetaine, amidazoliniumbetaine, sulfobetaine (INCI Sultaines) as well as the Phosphobetaine and alternatively meets formula I:

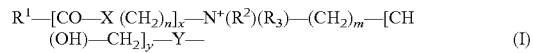

(I)

wherein $R^1$ is a saturated or unsaturated C6-22 alkyl residue, alternatively C8-18 alkyl residue, in particular a saturated C10-16 alkyl residue, for example a saturated C12-14 alkyl residue;

X is NH, NR$^4$ with C1-4 Alkyl residue R$^4$, O or S, n a number from 1 to 10, alternatively 2 to 5, in particular 3, x 0 or 1, alternatively 1, R$^2$, R$^3$ are independently a C1-4 alkyl residue, potentially hydroxy substituted such as a hydroxyethyl, alternatively a methyl.

m a number from 1 to 4, in particular 1, 2 or 3, y 0 or 1 and

Y is COO, SO3, OPO(OR$^5$)O or P(O)(OR$^5$)O, whereby R$^5$ is a hydrogen atom H or a C1-4 alkyl residue.

Suitable betaines are the alkyl betaines of the formula (Ia), the alkyl amido betaine of the formula (Ib), the Sulfo betaines of the formula (Ic) and the Amido sulfobetaine of the formula (Id);

(Ia)

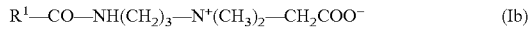

(Ib)

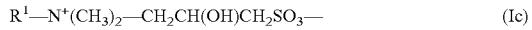

(Ic)

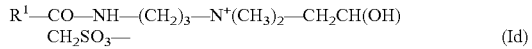

(Id)

in which R$^1$1 as the same meaning as in formula I. Suitable betaines are the Carbobetaine [wherein Y$^-$=COO$^-$], in particular the Carbobetaine of the formula (Ia) and (Ib), alternatively the Alkylamidobetaine of the formula (Ib).]

Examples of suitable betaines and sulfobetaine are the following [designated in accordance with INCI]: Almondamidopropyl of betaines, Apricotam idopropyl betaines, Avocadamidopropyl of betaines, Babassuamidopropyl of betaines, Behenam idopropyl betaines, Behenyl of betaines, betaines, Canolam idopropyl betaines, Capryl/Capram idopropyl betaines, Carnitine, Cetyl of betaines, Cocamidoethyl of betaines, Cocam idopropyl betaines, Cocam idopropyl Hydroxysultaine, Coco betaines, Coco Hydroxysultaine, Coco/Oleam idopropyl betaines, Coco Sultaine, Decyl of betaines, Dihydroxyethyl Oleyl Glycinate, Dihydroxyethyl Soy Glycinate, Dihydroxyethyl Stearyl Glycinate, Dihydroxyethyl Tallow Glycinate, Dimethicone Propyl of PG-betaines, Erucam idopropyl Hydroxysultaine, Hydrogenated Tallow of betaines, Isostearam idopropyl betaines, Lauram idopropyl betaines, Lauryl of betaines, Lauryl Hydroxysultaine, Lauryl Sultaine, Milkam idopropyl betaines, Minkamidopropyl of betaines, Myristam idopropyl betaines, Myristyl of betaines, Oleam idopropyl betaines, Oleam idopropyl Hydroxysultaine, Oleyl of betaines, Olivamidopropyl of betaines, Palmam idopropyl betaines, Palm itam idopropyl betaines, Palmitoyl Carnitine, Palm Kernelam idopropyl betaines, Polytetrafluoroethylene Acetoxypropyl of betaines, Ricinoleam idopropyl betaines, Sesam idopropyl betaines, Soyam idopropyl betaines, Stearam idopropyl betaines, Stearyl of betaines, Tallowam idopropyl betaines, Tallowam idopropyl Hydroxysultaine, Tallow of betaines, Tallow Dihydroxyethyl of betaines, Undecylenam idopropyl betaines and Wheat Germam idopropyl betaines. In one embodiment, the composition includes Cocam idopropyl betaines (Cocoamidopropylbetain).

3. Anionic surfactants

Suitable anionic surfactants to be used in the compositions and methods of the present invention are sulfates, sulfosuccinates, sulfoacetates, and/or sulfonates; alternatively alkyl sulfate and/or alkyl ethoxy sulfates; alternatively a combination of alkyl sulfates and/or alkyl ethoxy sulfates with a combined ethoxylation degree less than 5, alternatively less than 3, alternatively less than 2.

Sulphate or sulphonate surfactant is typically present at a level of at least 5%, alternatively from 5% to 40%, alternatively from 15% to 30%, alternatively at 15% to 25%, by weight of the liquid detergent composition.

Suitable sulphate or sulphonate surfactants for use in the compositions herein include water-soluble salts or acids of $C_{10}$-$C_{14}$ alkyl or hydroxyalkyl, sulphate or sulphonates. Suitable counterions include hydrogen, alkali metal cation or ammonium or substituted ammonium, but alternatively sodium. Where the hydrocarbyl chain is branched, it alternatively comprises $C_{1-4}$ alkyl branching units. The average percentage branching of the sulphate or sulphonate surfactant is alternatively greater than 30%, alternatively from 35% to 80%, alternatively from 40% to 60% of the total hydrocarbyl chains.

The sulphate or sulphonate surfactants may be selected from $C_{11}$-$C_{18}$ alkyl benzene sulphonates (LAS), $C_8$-$C_{20}$ primary, branched-chain and random alkyl sulphates (AS); $C_{10}$-$C_{18}$ secondary (2,3) alkyl sulphates; $C_{10}$-$C_{18}$ alkyl alkoxy sulphates (AE$_x$S) wherein alternatively x is from 1-30; $C_{10}$-$C_{18}$ alkyl alkoxy carboxylates alternatively comprising 1-5 ethoxy units; mid-chain branched alkyl sulphates as discussed in U.S. Pat. No. 6,020,303 and U.S. Pat. No. 6,060,443; mid-chain branched alkyl alkoxy sulphates as discussed in U.S. Pat. No. 6,008,181 and U.S. Pat. No. 6,020,303; modified alkylbenzene sulphonate (MLAS) as discussed in WO 99/05243, WO 99/05242, WO 99/05244, WO 99/05082, WO 99/05084, WO 99/05241, WO 99/07656, WO 00/23549, and WO 00/23548; methyl ester sulphonate (MES); and alpha-olefin sulphonate (AOS).

The paraffin sulphonates may be monosulphonates or disulphonates and usually are mixtures thereof, obtained by sulphonating paraffins of 10 to 20 carbon atoms. Suitable sulphonates are those of C12-18 carbon atoms chains and alternatively they are C14-17 chains. Paraffin sulphonates that have the sulphonate group(s) distributed along the paraffin chain are described in U.S. Pat. No. 2,503,280; U.S. Pat. No. 2,507,088; U.S. Pat. No. 3,260,744; U.S. Pat. No. 3,372,188 and in DE 735 096.

Also suitable are the alkyl glyceryl sulphonate surfactants and/or alkyl glyceryl sulphate surfactants described in WO06/014740: A mixture of oligomeric alkyl glyceryl sulfonate and/or sulfate surfactant selected from dimers, trimers, tetramers, pentamers, hexamers, heptamers, and mixtures thereof; wherein the weight percentage of monomers is from 0 wt % to 60 wt % by weight of the alkyl glyceryl sulfonate and/or sulfate surfactant mixture.

Other suitable anionic surfactants are alkyl, alternatively dialkyl sulfosuccinates and/or sulfoacetate. The dialkyl sulfosuccinates may be a $C_{6-15}$ linear or branched dialkyl sulfosuccinate. The alkyl moieties may be symmetrical (i.e., the same alkyl moieties) or asymmetrical (i.e., different alkyl moiety.es). Alternatively, the alkyl moiety is symmetrical.

Most common branched anionic alkyl ether sulphates are obtained via sulfation of a mixture of the branched alcohols and the branched alcohol ethoxylates. Also suitable are the sulfated fatty alcohols originating from the Fisher & Troshp reaction comprising up to 50% branching (40% methyl (mono or bi) 10% cyclohexyl) such as those produced from the safol™ alcohols from Sasol; sulfated fatty alcohols originating from the oxo reaction wherein at least 50 weight % of the alcohol is C2 isomer (methyl to pentyl) such as those produced from the Isalchem™ alcohols or Lial™ alcohols from Sasol; the sulfated fatty alcohols originating from the modified oxo reaction wherein at least 15 weight % of the alcohol is C2 isomer (methyl to pentyl) such as those produced from the Neodol™ alcohols from Shell.

4. Cationic Surfactants

Cationic surfactants, when present in the composition, are present in an effective amount, alternatively from 0.1% to 20%, by weight of the composition. Suitable cationic surfactants are quaternary ammonium surfactants. Suitable quaternary ammonium surfactants are selected from the group consisting of mono $C_6$-$C_{16}$, alternatively $C_6$-$C_{10}$ N-alkyl or alkenyl ammonium surfactants, wherein the remaining N positions are substituted by methyl, hydroxyehthyl or hydroxypropyl groups. Another suitable cationic surfactant is an $C_6$-$C_{18}$ alkyl or alkenyl ester of a quaternary ammonium alcohol, such as quaternary chlorine esters. Alternatively, the cationic surfactants have the formula (V):

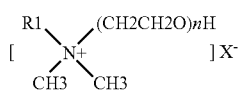

(V)

wherein R1 of formula (V) is $C_8$-$C_{18}$ hydrocarbyl and mixtures thereof, alternatively, $C_{8-14}$ alkyl, alternatively, $C_8$, $C_{10}$ or $C_{12}$ alkyl, and X of formula (V) is an anion, alternatively, chloride or bromide.

C. Cleaning Polymer

The composition of the present invention can further comprise one or more alkoxylated polyethyleneimine polymer. The composition may comprise from 0.01 wt % to 10 wt %, alternatively from 0.01 wt % to 2 wt %, alternatively from 0.1 wt % to 1.5 wt %, alternatively from 0.2% to 1.5%, by weight of the composition, of an alkoxylated polyethyleneimine polymer as described on page 2, line 33 to page 5, line 5 and exemplified in examples 1 to 4 at pages 5 to 7 of WO2007/135645.

The alkoxylated polyethyleneimine polymer of the present composition has a polyethyleneimine backbone having from 400 to 10000 weight average molecular weight, alternatively from 400 to 7000 weight average molecular weight, alternatively from 3000 to 7000 weight average molecular weight.

These polyamines can be prepared for example, by polymerizing ethyleneimine in presence of a catalyst such as carbon dioxide, sodium bisulfite, sulfuric acid, hydrogen peroxide, hydrochloric acid, acetic acid, and the like.

The alkoxylation of the polyethyleneimine backbone includes: (1) one or two alkoxylation modifications per nitrogen atom, dependent on whether the modification occurs at a internal nitrogen atom or at an terminal nitrogen atom, in the polyethyleneimine backbone, the alkoxylation modification consisting of the replacement of a hydrogen atom on a polyalkoxylene chain having an average of about 1 to about 40 alkoxy moieties per modification, wherein the terminal alkoxy moiety of the alkoxylation modification is capped with hydrogen, a $C_1$-$C_4$ alkyl or mixtures thereof; (2) a substitution of one $C_1$-$C_4$ alkyl moiety or benzyl moiety and one or two alkoxylation modifications per nitrogen atom, dependent on whether the substitution occurs at a internal nitrogen atom or at an terminal nitrogen atom, in the polyethyleneimine backbone, the alkoxylation modification consisting of the replacement of a hydrogen atom by a polyalkoxylene chain having an average of about 1 to about 40 alkoxy moieties per modification wherein the terminal alkoxy moiety is capped with hydrogen, a $C_1$-$C_4$ alkyl or mixtures thereof; or (3) a combination thereof.

The composition may further comprise the amphiphilic graft polymers based on water soluble polyalkylene oxides (A) as a graft base and sides chains formed by polymerization of a vinyl ester component (B), said polymers having an average of $\leq 1$ graft site per 50 alkylene oxide units and mean molar mass Mw of from 3,000 to 100,000 described in BASF patent application WO2007/138053 on pages 2 line 14 to page 10, line 34 and exemplified on pages 15-18.

D. Salts and Solvents

Salts and solvents are generally used to ensure preferred product quality for dissolution, thickness and aesthetics and to ensure better processing. When salts are included, the ions can be selected from magnesium, sodium, potassium, calcium, and/or magnesium and alternatively from sodium and magnesium, and are added as a hydroxide, chloride, acetate, sulphate, formate, oxide or nitrate salt to the compositions of the present invention. Salts are generally present at an active level of from 0.01% to 5%, alternatively from 0.015% to 3%, alternatively from 0.025% to 2.0%, by weight of the liquid detergent composition. In one embodiment, additional magnesium ions may be avoided.

Suitable solvents include C1-05 alcohols are according to the formula R—OH wherein R is a linear saturated alkyl group of from 1 to 5 carbon atoms, alternatively from 2 to 4. Suitable alcohols are ethanol, propanol, isopropanol or mixtures thereof. Other suitable alcohols are alkoxylated C1-8 alcohols according to the formula R (A0n-oh wherein R is a linear alkyl group of from 1 to 8 carbon atoms, alternatively from 3 to 6, wherein A is an alkoxy group alternatively propoxy and/or ethoxy and n is an integer of from 1 to 5, alternatively from 1 to 2. Suitable alcohols are buthoxy propoxy propanol (n-BPP), buthoxy Propanol (n-BP) buthoxyethanol or mixtures thereof. Suitable alkoxylated aromatic alcohols to be used herein are according to the formula R (B)n-OH whereinm R is an alkyl substituted or non alkyl substituted aryl group of from 1 to 20 carbon atoms, alternatively from 2 to 15 and alternatively from 2 to 10, wherein B is an alkoxy grup alternatively buthoxy, propoxy and/or ethoxy and n is an integer from of from 1 to 5, alternatively from 1 to 2. Suitable alkoxylated aromatic alcohols are benzoyethanol and or benzoypropanol. A suitable aromatic alcohol to be used herein is benzyl alcohol. Other suitable solvents include butyl diglycolether, benzylalcohol, propoxyporpoxypropanol (EP 0 859 044) ethers and diethers, glycols, alkoxylated glycols, $C_6$-$C_{16}$ glycol ethers, alkoxylated aromatic alcohols, aromatic alcohols, aliphatic branched alcohols, alkoxylated aliphatic branched alcohols, alkoxylated linear $C_1$-C5 alcohols, linear $C_1$-C5 alcohols, amines, $C_8$-$C_{14}$ alkyl and cycloalkyl hydrocarbons and halohydrocarbons, and mixtures thereof.

When present, the liquid detergent composition may contain from 0.01% to 20%, alternatively from 0.5% to 20%, alternatively from 1% to 10%, by weight of the composition, of a solvent. These solvents may be used in conjunction with an aqueous liquid carrier, such as water, or they may be used without any aqueous liquid carrier being present.

E. Hydrotrope

The dishwashing detergent compositions of the present invention may optionally comprise a hydrotrope in an effective amount so that the liquid detergent compositions are appropriately compatible in water. Suitable hydrotropes for use herein include anionic-type hydrotropes, particularly sodium, potassium, and ammonium xylene sulphonate, sodium, potassium and ammonium toluene sulphonate, sodium potassium and ammonium cumene sulphonate, and mixtures thereof, and related compounds, as disclosed in U.S. Pat. No. 3,915,903.

The compositions of the present invention typically comprise from 0% to 15% by weight of the liquid detergent composition of a hydrotropic, or mixtures thereof, alternatively from 1% to 10%, most alternatively from 3% to 6% by weight.

F. Polymeric Suds Stabilizer

The compositions of the present invention may optionally contain a polymeric suds stabilizer. These polymeric suds stabilizers provide extended suds volume and suds duration of the liquid detergent compositions. These polymeric suds stabilizers may be selected from homopolymers of (N,N-dialkylamino) alkyl esters and (N,N-dialkylamino) alkyl acrylate esters. The weight average molecular weight of the polymeric suds boosters, determined via conventional gel permeation chromatography, is from 1,000 to 2,000,000, alternatively from 5,000 to 1,000,000, alternatively from 10,000 to 750,000, alternatively from 20,000 to 500,000, even alternatively from 35,000 to 200,000. The polymeric suds stabilizer can optionally be present in the form of a salt, either an inorganic or organic salt, for example the citrate, sulphate, or nitrate salt of (N,N-dimethylamino)alkyl acrylate ester.

In one embodiment, the composition includes a suds stabilizer that is (N,N-dimethylamino)alkyl acrylate esters, namely the acrylate ester represented by the formula (VII):

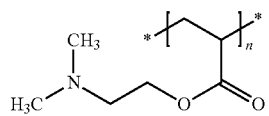

(VII)

Other suitable suds boosting polymers are copolymers of hydroxypropylacrylate/dimethyl aminoethylmethacrylate (copolymer of HPA/DMAM), represented by the formulae VIII and IX.

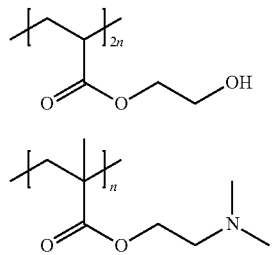

(VIII)

(IX)

When present in the compositions, the polymeric suds booster/stabilizer may be present in the composition from 0.01% to 15%, alternatively from 0.05% to 10%, alternatively from 0.1% to 5%, by weight of the composition.

Another suitable class of polymeric suds booster polymers are hydrophobically modified cellulosic polymers having a number average molecular weight (Mw) below 45,000; alternatively between 10,000 and 40,000; alternatively between 13,000 and 25,000. The hydrophobically modified cellulosic polymers include water soluble cellulose ether derivatives, such as nonionic and cationic cellulose derivatives. In one embodiment, the composition includes methylcellulose, hydroxypropyl methylcellulose, hydroxyethyl methylcellulose, or mixtures thereof.

G. Diamines

Another optional ingredient in the composition of the present invention is a diamine. Since the habits and practices of the users of liquid detergent compositions show considerable variation, the composition will alternatively contain 0% to 15%, alternatively 0.1% to 15%, alternatively 0.2% to 10%, alternatively 0.25% to 6%, alternatively 0.5% to 1.5% by weight of said composition, of at least one diamine.

Suitable organic diamines are those in which pK1 and pK2 are in the range of 8.0 to 11.5, alternatively in the range of 8.4 to 11, even alternatively from 8.6 to 10.75. Suitable materials include 1,3-bis(methylamine)-cyclohexane (pKa=10 to 10.5), 1,3 propane diamine (pK1=10.5; pK2=8.8), 1,6 hexane diamine (pK1=11; pK2=10), 1,3 pentane diamine (DYTEK EPO) (pK1=10.5; pK2=8.9), 2-methyl 1,5 pentane diamine (DYTEK A®) (pK1=11.2; pK2=10.0). Other suitable materials include primary/primary diamines with alkylene spacers ranging from $C_4$ to $C_8$. In general, it is believed that primary diamines are preferred over secondary and tertiary diamines. pKa is used herein in the same manner as is commonly known to people skilled in the art of chemistry: in an all-aqueous solution at 25° C. and for an ionic strength between 0.1 to 0.5 M. Values referenced herein can be obtained from literature, such as from "Critical Stability Constants: Volume 2, Amines" by Smith and Martel, Plenum Press, NY and London, 1975.

H. Carboxylic Acid

The dishwashing detergent compositions of the present invention may comprise a linear or cyclic carboxylic acid or salt thereof to improve the rinse feel of the composition. The presence of anionic surfactants, especially when present in higher amounts in the region of 15-35% by weight of the composition, results in the composition imparting a slippery feel to the hands of the user and the dishware.

Carboxylic acids useful herein include $C_{1-6}$ linear or at least 3 carbon containing cyclic acids. The linear or cyclic carbon-containing chain of the carboxylic acid or salt thereof may be substituted with a substituent group selected from the group consisting of hydroxyl, ester, ether, aliphatic groups having from 1 to 6, alternatively 1 to 4 carbon atoms, and mixtures thereof.

Suitable carboxylic acids are those selected from the group consisting of salicylic acid, maleic acid, acetyl salicylic acid, 3 methyl salicylic acid, 4 hydroxy isophthalic acid, dihydroxyfumaric acid, 1,2, 4 benzene tricarboxylic acid, pentanoic acid and salts thereof, citric acid and salts thereof, and mixtures thereof. Where the carboxylic acid exists in the salt form, the cation of the salt is alternatively selected from alkali metal, alkaline earth metal, monoethanolamine, diethanolamine or triethanolamine and mixtures thereof.

The carboxylic acid or salt thereof, when present, is present at the level of from 0.1% to 5%, alternatively from 0.2% to 1%, alternatively from 0.25% to 0.5%, by weight of the compositian.

I. Malodor Control Component

The dishwashing detergent composition comprises a malodor control component. The malodor control component may include at least one volatile aldehyde and an acid catalyst. The malodor control component is designed to deliver genuine malodor neutralization and not function merely by covering up or masking odors. A genuine malodor neutralization provides a sensory and analytically measurable (e.g. gas chromatograph) malodor reduction. Thus, if the malodor control component delivers a genuine malodor neutralization, the composition will reduce malodors in the vapor and/or liquid phase.

1. Volatile Aldehydes

The malodor control component includes a mixture of volatile aldehydes that neutralize malodors in vapor and/or liquid phase via chemical reactions. Such volatile aldehydes are also called reactive aldehydes (RA). Volatile aldehydes may react with amine-based odors, following the path of Schiff-base formation. Volatiles aldehydes may also react with sulfur-based odors, forming thiol acetals, hemi thiolacetals, and thiol esters in vapor and/or liquid phase. It may be desirable for these vapor and/or liquid phase volatile aldehydes to have virtually no negative impact on the desired perfume character of a product. Aldehydes that are partially volatile may be considered a volatile aldehyde as used herein.

Suitable volatile aldehydes may have a vapor pressure (VP) in the range of about 0.0001 torr to 100 torr, alternatively about 0.0001 torr to about 10 torr, alternatively about 0.001 torr to about 50 torr, alternatively about 0.001 torr to about 20 torr, alternatively about 0.001 torr to about 0.100 torr, alternatively about 0.001 torr to 0.06 torr, alternatively about 0.001 torr to 0.03 torr, alternatively about 0.005 torr to about 20 torr, alternatively about 0.01 torr to about 20 torr, alternatively about 0.01 torr to about 15 torr, alternatively about 0.01 torr to about 10 torr, alternatively about 0.05 torr to about 10 torr, measured at 25° C.

The volatile aldehydes may also have a certain boiling point (B.P.) and octanol/water partition coefficient (P). The boiling point referred to herein is measured under normal standard pressure of 760 mmHg The boiling points of many volatile aldehydes, at standard 760 mm Hg are given in, for example, "Perfume and Flavor Chemicals (Aroma Chemicals)," written and published by Steffen Arctander, 1969.

The octanol/water partition coefficient of a volatile aldehyde is the ratio between its equilibrium concentrations in octanol and in water. The partition coefficients of the volatile aldehydes used in the malodor control component may be more conveniently given in the form of their logarithm to the base 10, logP. The logP values of many volatile aldehydes have been reported. See, e.g., the Pomona92 database, available from Daylight Chemical Information Systems, Inc. (Daylight CIS), Irvine, Calif. However, the logP values are most conveniently calculated by the "CLOGP" program, also available from Daylight CIS. This program also lists experimental logP values when they are available in the Pomona92 database. The "calculated logP" (ClogP) is determined by the fragment approach of Hansch and Leo (cf., A. Leo, in Comprehensive Medicinal Chemistry, Vol. 4, C. Hansch, P. G. Sammens, J. B. Taylor and C. A. Ramsden, Eds., p. 295, Pergamon Press, 1990). The fragment approach is based on the chemical structure of each volatile aldehyde, and takes into account the numbers and types of atoms, the atom connectivity, and chemical bonding. The ClogP values, which are the most reliable and widely used estimates for this physicochemical property, are alternatively used instead of the experimental logP values in the selection of volatile aldehydes for the malodor control component.

The ClogP values may be defined by four groups and the volatile aldehydes may be selected from one or more of these groups. The first group comprises volatile aldehydes that have a B.P. of about 250° C. or less and ClogP of about 3 or less. The second group comprises volatile aldehydes that have a B.P. of 250° C. or less and ClogP of 3.0 or more. The third group comprises volatile aldehydes that have a B.P. of 250° C. or more and ClogP of 3.0 or less. The fourth group comprises volatile aldehydes that have a B.P. of 250° C. or more and ClogP of 3.0 or more. The malodor control component may comprise any combination of volatile aldehydes from one or more of the ClogP groups.

In some embodiments, the malodor control component of the present invention may comprise, by total weight of the malodor control component, from about 0% to about 30% of volatile aldehydes from group 1, alternatively about 25%; and/or about 0% to about 10% of volatile aldehydes from group 2, alternatively about 10%; and/or from about 10% to about 30% of volatile aldehydes from group 3, alternatively about 30%; and/or from about 35% to about 60% of volatile aldehydes from group 4, alternatively about 35%.

Exemplary volatile aldehydes which may be used in a malodor control component include, but are not limited to, Adoxal (2,6,10-Trimethyl-9-undecenal), Bourgeonal (4-t-butylbenzenepropionaldehyde), Lilestralis 33 (2-methyl-4-t-butylphenyl)propanal), Cinnamic aldehyde, cinnamaldehyde (phenyl propenal, 3-phenyl-2-propenal), Citral, Geranial, Neral (dimethyloctadienal, 3,7-dimethyl-2,6-octadien-1-al), Cyclal C (2,4-dimethyl-3-cyclohexen-1-carbaldehyde), Florhydral (3-(3-Isopropyl-phenyl)-butyraldehyde), Citronellal (3,7-dimethyl 6-octenal), Cymal, cyclamen aldehyde, Cyclosal, Lime aldehyde (Alpha-methyl-p-isopropyl phenyl propyl aldehyde), Methyl Nonyl Acetaldehyde, aldehyde C12 MNA (2-methyl-1-undecanal), Hydroxycitronellal, citronellal hydrate (7-hydroxy-3,7-dimethyl octan-1-al), Helional (alpha-methyl-3,4-(methylenedioxy)-hydrocinnamaldehyde, hydrocinnamaldehyde (3-phenylpropanal, 3-phenylpropionaldehyde), Intreleven aldehyde (undec-10-en-1-al), Ligustral, Trivertal (2,4-dimethyl-3-cyclohexene-1-carboxaldehyde), Jasmorange, satinaldehyde (2-methyl-3-tolylproionaldehyde, 4-dimethylbenzenepropanal), Lyral (4-(4-hydroxy-4-methyl pentyl)-3-cyclohexene-1-carboxaldehyde), Melonal (2,6-Dimethyl-5-Heptenal), Methoxy Melonal (6-methoxy-2,6-dimethylheptanal), methoxycinnamaldehyde (trans-4-methoxycinnamaldehyde), Myrac aldehyde isohexenyl cyclohexenyl-carboxaldehyde, trifernal ((3-methyl-4-phenyl propanal, 3-phenyl butanal), lilial, P.T. Bucinal, lysmeral, benzenepropanal (4-tert-butyl-alpha-methyl-hydrocinnamaldehyde), Dupical, tricyclodecylidenebutanal (4-Triyclo5210-2,6decylidene-8butanal), Melafleur (1,2,3,4,5,6,7,8-octahydro-8,8-dimethyl-2-naphthaldehyde), Methyl Octyl Acetaldehyde, aldehyde C-11 MOA (2-mehtyl deca-1-al), Onicidal (2,6,10-trimethyl-5,9-undecadien-1-al), Citronellyl oxyacetaldehyde, Muguet aldehyde 50 (3,7-dimethyl-6-octenyl) oxyacetaldehyde), phenylacetaldehyde, Mefranal (3-methyl-5-phenyl pentanal), Triplal, Vertocitral dimethyl tetrahydrobenzene aldehyde (2,4-dimethyl-3-cyclohexene-1-carboxaldehyde), 2-phenylproprionaldehyde, Hydrotropaldehyde, Canthoxal, anisylpropanal 4-methoxy-alpha-methyl benzenepropanal (2-anisylidene propanal), Cylcemone A (1,2,3,4,5,6,7,8-octahydro-8,8-dimethyl-2-naphthaldehyde), and Precylcemone B (1-cyclohexene-1-carboxaldehyde).

Still other exemplary aldehydes include, but are not limited to, acetaldehyde (ethanal), pentanal, valeraldehyde, amylaldehyde, Scentenal (octahydro-5-methoxy-4,7-Methano-1 H-indene-2-carboxaldehyde), propionaldehyde (propanal), Cyclocitral, beta-cyclocitral, (2,6,6-trimethyl-1-cyclohexene-1-acetaldehyde), Iso Cyclocitral (2,4,6-trimethyl-3-cyclohexene-1-carboxaldehyde), isobutyraldehyde, butyraldehyde, isovaleraldehyde (3-methyl butyraldehyde), methylbutyraldehyde (2-methyl butyraldehyde, 2-methyl butanal), Dihydrocitronellal (3,7-dimethyl octan-1-al), 2-Ethylbutyraldehyde, 3-Methyl-2-butenal, 2-Methylpentanal, 2-Methyl Valeraldehyde, Hexenal (2-hexenal, trans-2-hexenal), Heptanal, Octanal, Nonanal, Decanal, Lauric aldehyde, Tridecanal, 2-Dodecanal, Methylthiobutanal, Glutaraldehyde, Pentanedial, Glutaric aldehyde, Heptenal, cis or trans-Heptenal, Undecenal (2-, 10-), 2,4-octadienal, Nonenal (2-, 6-), Decenal (2-, 4-), 2,4-hexadienal, 2,4-Decadienal, 2,6-Nonadienal, Octenal, 2,6-dimethyl 5-heptenal, 2-isopropyl-5-methyl-2-hexenal, Trifernal, beta methyl Benzenepropanal, 2,6,6-Trimethyl-1-cyclohexene-1-acetaldehyde, phenyl Butenal (2-phenyl 2-butenal), 2.Methyl-3(p-isopropylphenyl)-propionaldehyde, 3-(p-isopropylphenyl)-propionaldehyde, p-Tolylacetaldehyde (4-methylphenylacetaldehyde), Anisaldehyde (p-methoxybenzene aldehyde), Benzaldehyde, Vernaldehyde (1-Methyl-4-(4-methylpentyl)-3-cyclohexenecarbaldehyde), Heliotropin (piperonal) 3,4-Methylene dioxy benzaldehyde, alpha-Amylcinnamic aldehyde, 2-pentyl-3-phenylpropenoic aldehyde, Vanillin (4-methoxy 3-hydroxy benzaldehyde), Ethyl vanillin (3-ethoxy 4-hydroxybenzaldehyde), Hexyl Cinnamic aldehyde, Jasmonal H (alpha-n-hexyl-cinnamaldehyde), Floralozone, (para-ethyl-alpha,alpha-dimethyl Hydrocinnamaldehyde), Acalea (p-methyl-alpha-pentylcinnamaldehyde), methylcinnamaldehyde, alpha-Methylcinnamaldehyde (2-methyl 3-pheny propenal), alpha-hexylcinnamaldehyde (2-hexyl 3-phenyl propenal), Salicylaldehyde (2-hydroxy benzaldehyde), 4-ethyl benzaldehyde, Cuminaldehyde (4-isopropyl benzaldehyde), Ethoxybenzaldehyde, 2,4-dimethylbenzaldehyde, Veratraldehyde (3,4-dimethoxybenzaldehyde), Syringaldehyde (3,5-dimethoxy 4-hydroxybenzaldehyde), Catechaldehyde (3,4-dihydroxybenzaldehyde), Safranal (2,6,6-trimethyl-1,3-diene methanal), Myrtenal (pin-2-ene-1-carbaldehyde), Perillaldehyde L-4(1-methylethenyl)-1-cyclohexene-1-methylpentenal, carboxaldehyde), 2,4-Dimethyl-3-cyclohexene carboxaldehyde, 2-Methyl-2-pentenal, 2-pyruvaldehyde, formyl Tricyclodecan, Mandarin aldehyde, Cyclemax, Pino acetaldehyde, Corps Iris, Maceal, and Corps 4322.

In one embodiment, the malodor control component includes a mixture of two or more volatile aldehydes selected from the group consisting of 2-ethoxy Benzylaldehyde, 2-isopropyl-5-methyl-2-hexenal, 5-methyl Furfural, 5-methyl-thiophene-carboxaldehyde, Adoxal, p-anisaldehyde, Benzylaldehyde, Bourgenal, Cinnamic aldehyde, Cymal, Decyl aldehyde, Floral super, Florhydral, Helional, Lauric aldehyde, Ligustral, Lyral, Melonal, o-anisaldehyde, Pino acetaldehyde, P.T. Bucinal, Thiophene carboxaldehyde, trans-4-Decenal, trans trans 2,4-Nonadienal, Undecyl aldehyde, and mixtures thereof.

In some embodiments, the malodor control component includes fast reacting volatile aldehydes. "Fast reacting volatile aldehydes" refers to volatile aldehydes that either (1) reduce amine odors by 20% or more in less than 40 seconds; or (2) reduce thiol odors by 20% or more in less than 30 minutes.

In one embodiment, the malodor control component includes a mixture of the volatile aldehydes listed in Table 1 and referred to herein as Accord A.

TABLE 1

Accord A

| Material | Wt. % | CAS Number | ClogP Group | VP (torr) @ 25° C. |
|---|---|---|---|---|
| Intreleven Aldehyde | 5.000 | 112-45-8 | 3 | 0.060 |
| Florhydral | 10.000 | 125109-85-5 | 4 | 0.008 |
| Floral Super | 25.000 | 71077-31-1 | 3 | 0.030 |
| Scentenal | 10.000 | 86803-90-9 | 2 | 0.010 |
| Cymal | 25.000 | 103-95-7 | 4 | 0.007 |
| o-anisaldehyde | 25.000 | 135-02-4 | 1 | 0.032 |

In another embodiment, the malodor control component includes a mixture of the volatile aldehydes listed in Table 2 and referred to herein as Accord B.

TABLE 2

Accord B

| Material | Wt. % | CAS Number | ClogP Group | VP (torr) @ 25° C. |
|---|---|---|---|---|
| Intreleven Aldehyde | 2.000 | 112-45-8 | 3 | 0.060 |
| Florhydral | 20.000 | 125109-85-5 | 4 | 0.008 |
| Floral Super | 10.000 | 71077-31-1 | 3 | 0.030 |
| Scentenal | 5.000 | 86803-90-9 | 2 | 0.010 |
| Cymal | 25.000 | 103-95-7 | 4 | 0.007 |
| Floralozone | 10.000 | 67634-14-4 | 4 | 0.005 |
| Adoxal | 1.000 | 141-13-9 | 4 | 0.007 |
| Methyl Nonyl Acetaldehyde | 1.000 | 110-41-8 | 3 | 0.030 |
| Melonal | 1.000 | 106-72-9 | 3 | 0.670 |
| o-anisaldehyde | 25.000 | 135-02-4 | 1 | 0.032 |

In another embodiment, the malodor control component includes a mixture of about 71.2% volatile aldehydes, the remainder being other an ester and an alcohol perfume raw material. This mixture is listed in Table 3 and referred to herein as Accord C.

TABLE 3

Accord C

| Material | Wt. % | CAS Number | ClogP Group | VP (torr) @ 25° C. |
|---|---|---|---|---|
| Intreleven Aldehyde | 2.000 | 112-45-8 | 3 | 0.060 |
| Florhydral | 10.000 | 125109-85-5 | 4 | 0.008 |
| Floral Super | 5.000 | 71077-31-1 | 3 | 0.030 |
| Scentenal | 2.000 | 86803-90-9 | 2 | 0.010 |
| Cymal | 15.000 | 103-95-7 | 4 | 0.007 |
| Floralozone | 12.000 | 67634-14-4 | 4 | 0.005 |
| Adoxal | 1.000 | 141-13-9 | 4 | 0.007 |
| Methyl Nonyl Acetaldehyde | 1.000 | 110-41-8 | 3 | 0.030 |
| Melonal | 1.000 | 106-72-9 | 3 | 0.670 |
| Flor Acetate | 11.800 | 5413-60-5 | 1 | 0.060 |
| Frutene | 7.000 | 17511-60-3 | 4 | 0.020 |
| Helional | 5.000 | 1205-17-0 | 2 | 0.0005 |
| Bourgeonal | 2.000 | 18127-01-0 | 4 | 0.004 |
| Linalool | 10.000 | 78-70-6 | 3 | 0.050 |
| Benzaldehyde | 0.200 | 100-52-7 | 1 | 1.110 |
| o-anisaldehyde | 15.000 | 135-02-4 | 1 | 0.320 |

Accords A, B, or C can be formulated in with other perfume raw materials in an amount, for example, of about 10% by weight of the malodor control component. Additionally, the individual volatile aldehydes or a various combination of the volatile aldehydes can be formulated into a malodor control component. In certain embodiments, the volatile aldehydes may be present in an amount up to 100%, by weight of the malodor control component, alternatively from 1% to about 100%, alternatively from about 2% to about 100%, alternatively from about 3% to about 100%, alternatively about 50% to about 100%, alternatively about 70% to about 100%, alternatively about 80% to about 100%, alternatively from about 1% to about 20%, alternatively from about 1% to about 10%, alternatively from about 1% to about 5%, alternatively from about 1% to about 3%, alternatively from about 2% to about 20%, alternatively from about 3% to about 20%, alternatively from about 4% to about 20%, alternatively from about 5% to about 20%, by weight of the composition.

In some embodiments where volatility is not important for neutralizing a malodor, the present invention may include poly-aldehydes, for example, di-, tri-, tetra-aldehydes. Such embodiments may include laundry detergents, additive, and the like for leave-on, through the wash, and rinse-off type of applications.

2. Acid Catalyst

The malodor control component of the present invention may include an effective amount of an acid catalyst to neutralize sulfur-based malodors. It has been found that certain mild acids have an impact on aldehyde reactivity with thiols in the liquid and vapor phase. It has been found that the reaction between thiol and aldehyde is a catalytic reaction that follows the mechanism of hemiacetal and acetal formation path. When the present malodor control component contains an acid catalyst and contacts a sulfur-based malodor, the volatile aldehyde reacts with thiol. This reaction may form a thiol acetal compound, thus, neutralizing the sulfur-based odor. Without an acid catalyst, only hemi-thiol acetal is formed.

Suitable acid catalysts have a VP, as reported by Scifinder, in the range of about 0.001 torr to about 38 torr, measured at 25° C., alternatively about 0.001 torr to about 14 torr, alternatively from about 0.001 to about 1, alternatively from about 0.001 to about 0.020, alternatively about 0.005 to about 0.020, alternatively about 0.010 to about 0.020.

The acid catalyst may be a weak acid. A weak acid is characterized by an acid dissociation constant, $K_a$, which is an equilibrium constant for the dissociation of a weak acid; the pKa being equal to minus the decimal logarithm of $K_a$. The acid catalyst may have a pKa from about 4.0 to about 6.0, alternatively from about 4.3 and 5.7, alternatively from about 4.5 to about 5, alternatively from about 4.7 to about 4.9. Suitable acid catalyst include those listed in Table 4.

TABLE 4

| Material | VP (torr) @ 25° C. |
| --- | --- |
| Formic Acid | 36.5 |
| Acetic Acid | 13.9 |
| Trimethyl Acetic Acid | 0.907 |
| Phenol (alkaline in liquid apps yet acidic in vapor phase) | 0.610 |
| Tiglic acid | 0.152 |
| Caprylic acid | 0.0222 |
| 5-Methyl thiophene carboxylic acid | 0.019 |
| Succinic acid | 0.0165 |
| Benzoic acid | 0.014 |
| Mesitylenic acid | 0.00211 |

Depending on the desired use of the malodor control component, one may consider the scent character or the affect on the scent of the malodor control component when selecting an acid catalyst. In some embodiments of the malodor control component, it may be desirable to select an acid catalyst that provides a neutral to pleasant scent. Such acid catalysts may have a VP of about 0.001 torr to about 0.020 torr, measured at 25° C., alternatively about 0.005 torr to about 0.020 torr, alternatively about 0.010 torr to about 0.020 torr Non-limiting examples of such acid catalyst include 5-methyl thiophene carboxaldehyde with carboxylic acid impurity, succinic acid, or benzoic acid.

The malodor control component may include about 0.05% to about 5%, alternatively about 0.1% to about 1.0%, alternatively about 0.1% to about 0.5%, alternatively about 0.1% to about 0.4%, alternatively about 0.4% to about 1.5%, alternatively about 0.4% of an acid catalyst by weight of the malodor control component.

In an acetic acid system, the present malodor control component may include about 0.4% of acetic acid (50:50 TC:DPM, 0.4% acetic acid).

TABLE 5

| Sample Formulated | Actual % acetic acid in DPM | % Butanethiol reduction @ 30 min. |
| --- | --- | --- |
| 50:50 TC:DPM 0% Acetic Acid | 0.00 | 12.00 |
| 50:50 TC:DPM 0.05% Acetic Acid | 0.04 | 14.65 |
| 50:50 TC:DPM 0.1% Acetic Acid | 0.10 | 25.66 |
| 50:50 TC:DPM 0.2% Acetic Acid | 0.42 | 34.68 |
| 50:50 TC:DPM 0.5% Acetic Acid | 1.00 | 24.79 |
| 50:50 TC:DPM 1.0% Acetic Acid | 2.00 | 7.26 |

When an acid catalyst is present with a volatile aldehyde (or RA), the acid catalyst may increase the efficacy of the volatile aldehyde on malodors in comparison to the malodor efficacy of the volatile aldehyde on its own. For example, 1% volatile aldehyde and 1.5% benzoic acid provides malodor removal benefit equal to or better than 5% volatile aldehyde alone.

The malodor control component may have a pH from about 3 to about 8, alternatively from about 4 to about 7, alternatively from about, alternatively from about 4 to about 6.

J. Other Optional Components:

The dishwashing detergent compositions herein can further comprise a number of other optional ingredients suitable for use in liquid detergent compositions such as diluents, including dipropylene glycol methyl ether, and 3-methoxy-3-methyl-1-butanol, and mixtures thereof; dyes; pearlescent agents; opacifiers; enzymes; thickening agents; preservatives; disinfecting agents; and pH buffering means so that the liquid detergent compositions herein generally have a pH of from 3 to 14, alternatively 6 to 13, alternatively 8 to 11. The pH of the composition can be adjusted using pH modifying ingredients known in the art.

The malodor control component may also include odor masking agents, odor blocking agents, and/or diluents. For example, the composition may include a chelant, surfactant, and malodor control components comprising a mixture of volatile aldehydes for neutralizing a malodor, perfume ionones, and a diluent. Alternatively, the malodor control component may include 100% volatile aldehydes.

"Odor-masking agents" refer to known compounds (e.g. perfume raw materials) that mask or hide a malodorous compound. Odor-masking may include a compound with a non-offensive or pleasant smell that is dosed such it limits the ability to sense a malodorous compound. Odor-masking may involve the selection of compounds which coordinate with an anticipated malodor to change the perception of the overall scent provided by the combination of odorous compounds. "Odor blocking agents" refer to known compounds that dull the human sense of smell.

The composition may also include perfume raw materials that solely provide a hedonic benefit (i.e. that do not neutralize malodors yet provide a pleasant fragrance). Suitable perfumes are disclosed in U.S. Pat. No. 6,248,135, which is incorporated in its entirety by reference.

K. Viscosity

The composition of the present invention may have viscosity from 50 to 2000 centipoises (50-2000 mPa*s), alternatively from 100 to 1500 centipoises (100-1500 mPa*s), alternatively from 500 to 1300 centipoises (500-1300 mPa*s) at $20^{s-1}$ and 20° C. Viscosity can be determined by conventional methods.

Viscosity according to the present invention is measured using an AR 550 rheometer from TA instruments using a plate steel spindle at 40 mm diameter and a gap size of 500 μm. The high shear viscosity at $20^{s-1}$ and low shear viscosity at $0.05^{s-1}$ can be obtained from a logarithmic shear rate sweep from $0.1^{s-1}$ to $25^{s-1}$ in 3 minutes time at 20° C. The preferred rheology described therein may be achieved using internal existing structuring with detergent ingredients or by employing an external rheology modifier. Hence, in one embodiment of the present invention, the composition comprises further a rheology modifier.

II. Method of Cleaning/Treating a Dishware

The method of the present invention comprises cleaning dishware with a dishwashing detergent composition comprising a cleaning agent and malodour control component. The dishwashing operation comprises the steps of applying said composition onto said dishware, typically in diluted or neat form and rinsing said composition from said dishware or said surface, or leaving the composition to dry on said surface without rinsing said dishware or said surface. Instead of leaving said composition to dry on said surface on the air, it can also be hand-dried using a kitchen towel. During the dishwashing operation, particularly during the application of the composition to the dishware and/or rinsing away of said composition from the dishware, the hands and skin of the user may be exposed to the composition in diluted or neat form.

By "in its neat form", it is meant herein that the composition is applied directly onto the surface to be treated without undergoing any dilution by the user (immediately) prior to the application. This direct application of that said composition onto the surface to be treated can be achieved through direct squeezing of that said composition out of the hand dishwashing liquid bottle onto the surface to be cleaned, or through squeezing that said composition out of the hand dishwashing liquid bottle on a pre-wetted or non pre-wetted cleaning article, such as without intending to be limiting a sponge, a cloth or a brush, prior to cleaning the targeted surface with said cleaning article, By "diluted form", it is meant herein that said composition is diluted by the user with an appropriate solvent, typically with water. By "rinsing", it is meant herein contacting the dishware cleaned with the process according to the present invention with substantial quantities of appropriate solvent, typically water, after the step of applying the composition herein onto said dishware. By "substantial quantities", it is meant usually 0.1 to 20 liters.

In one embodiment of the present invention, the composition herein can be applied in its diluted form. Soiled dishes are contacted with an effective amount, typically from 0.5 ml to 20 ml (per 25 dishes being treated), alternatively from 3 ml to 10 ml, of the liquid detergent composition of the present invention diluted in water. The actual amount of liquid detergent composition used will be based on the judgment of user, and will typically depend upon factors such as the particular product formulation of the composition, including the concentration of active ingredients in the composition, the number of soiled dishes to be cleaned, the degree of soiling on the dishes, and the like. The particular product formulation, in turn, will depend upon a number of factors, such as the intended market (i.e., U.S., Europe, Japan, etc.) for the composition product. Typical light-duty detergent compositions are described in the examples section.

Generally, from 0.01 ml to 150 ml, alternatively from 3 ml to 40 ml, alternatively from 3 ml to 10 ml of a detergent composition of the invention is combined with from 2000 ml to 20000 ml, more typically from 5000 ml to 15000 ml of water in a sink having a volumetric capacity in the range of from 1000 ml to 20000 ml, more typically from 5000 ml to 15000 ml. The soiled dishes are immersed in the sink containing the diluted compositions then obtained, where contacting the soiled surface of the dish with a cloth, sponge, or similar article cleans them. The cloth, sponge, or similar article may be immersed in the detergent composition and water mixture prior to being contacted with the dish surface, and is typically contacted with the dish surface for a period of time ranged from 1 to 10 seconds, although the actual time will vary with each application and user. The contacting of cloth, sponge, or similar article to the dish surface is alternatively accompanied by a concurrent scrubbing of the dish surface.

Another method of the present invention will comprise immersing the soiled dishes into a water bath or held under running water without any liquid dishwashing detergent. A device for absorbing liquid dishwashing detergent, such as a sponge, is placed directly into a separate quantity of a concentrated pre-mix of diluted liquid dishwashing detergent, for a period of time typically ranging from 1 to 5 seconds. The absorbing device, and consequently the diluted liquid dishwashing composition, is then contacted individually to the surface of each of the soiled dishes to remove said soiling. The absorbing device is typically contacted with each dish surface for a period of time range from 1 to 10 seconds, although the actual time of application will be dependent upon factors such as the degree of soiling of the dish. The step of contacting of the absorbing device to the dish surface is alternatively accompanied by concurrent scrubbing. Typically, said concentrated pre-mix of diluted liquid dishwashing detergent is formed by combining 1ml to 200 ml of neat dishwashing detergent with 50 ml to 1500 ml of water, more typically from 200 ml to 1000 ml of water.

III. Packaging

The detergent compositions of the present invention may be packaged in any suitable packaging for delivering the liquid detergent composition for use. Alternatively the package is a clear package made of glass or plastic.

EXAMPLES

The examples herein are meant to exemplify the present invention but are not necessarily used to limit or otherwise define the scope of the present invention. All numerical values in the below examples are weight %, by total weight of the composition unless otherwise stated.

|  | Ex. 1 | Ex. 2 | Ex. 3 | Ex. 4 | Ex. 5 | Ex. 6 | Ex. 7 |
|---|---|---|---|---|---|---|---|
| Alkyl Ethoxy Sulfate AExS* | 22.5 | 25.0 | 25.0 | 27.0 | 20.0 | 22.5 | 22.5 |
| w % linear in alkyl chain | 45 | 84 | 70 | 50 | 76 | 76 | 40 |
| w % branching in alkyl chain | 55 | 16 | 30 | 50 | 24 | 24 | 60 |
| Amine oxide | 8.0 | 6.0 | 7.0 | 5.0 | 5.0 | 8.0 | 7.0 |
| Nonionic |  |  |  |  |  |  |  |
| C9-11 EO8 (15% branching) | 7.0 | — | — | 3.0 | 5.0 | — | 4.0 |
| Ethylan 1008 (100% branching) | — | — | 3.0 | — | — | 7.0 | — |

-continued

|  |  |  |  |  |  |  |  |
|---|---|---|---|---|---|---|---|
| Lutensol TO7 (100% branching) | — | 7.0 | — | — | 5.0 | — | 3.0 |
| GLDA¹ | 1.0 | — | — | — | 1.0 | 0.5 | 0.8 |
| DTPMP² | — | 1.0 | — | — | 0.5 | — | 0.4 |
| DTPA³ | — | — | 1.0 | — | — | — | — |
| MGDA⁴ | — | — | — | 1.0 | — | 0.5 | — |
| Sodium Citrate | — | — | 1.0 | — | 0.5 | 0.8 | — |
| Solvent: ethanol, isopropylalcohol, . . . | 2.5 | 7.0 | 4.0 | 3.0 | 2.0 | 3.0 | 2.5 |
| Polypropylene glycol MW2000 | 1.0 | 1.5 | 0.5 | 1.0 | — | 2.0 | 1.0 |
| Sodium Chloride | 0.5 | 0.8 | 1.0 | 1.0 | 0.5 | 0.5 | 0.5 |
| Average branching weight % in total surfactant mixture | 35.8 | 28.9 | 30.0 | 39.8 | 30.1 | 33 | 46.8 |
| Total Surfactant/Nonionic weight ratio | 5.3 | 5.4 | 11.6 | 11.7 | 3.5 | 5.4 | 5.2 |

|  | Ex. 8 | Ex. 9 | Ex. 10 | Ex. 11 |
|---|---|---|---|---|
| Alkyl Ethoxy Sulfate AExS* | 13 | 16 | 17 | 15 |
| w % linear in alkyl chain | 70 | 60 | 84 | 45 |
| w % branching in alkyl chain | 30 | 40 | 16 | 55 |
| Amine oxide | 4.5 | 5.5 | 6.0 | 5.0 |
| Nonionic |  |  |  |  |
| C9-11 EO8 (15% branching) | — | 2.0 | — | 5 |
| Ethylan 1008 (100% branching) | — | 2.0 | — | — |
| Lutensol TO7 (100% branching) | 4 | — | 5 | — |
| GLDA¹ | 0.7 | 0.4 | 0.7 | 0.7 |
| DTPMP² | — | 0.3 | — | — |
| Sodium Citrate | — | — | 0.2 | — |
| Solvent: ethanol, isopropylalcohol, . . . | 2.0 | 2.0 | 2.0 | 1.0 |
| Polypropylene glycol MW 2000 | 0.5 | 0.3 | 0.5 | 0.4 |
| Salt: Sodium Chloride | 0.5 | 0.8 | 0.4 | 0.5 |
| Average branching weight % in total surfactant mixture | 17.3 | 14.9 | 12.4 | 36.0 |
| Total surfactant/Nonionic weight ratio | 5.4 | 6.4 | 5.6 | 5.0 |

|  | Ex. 12 | Ex. 13 | Ex. 14 | Ex. 15 | Ex. 16 |
|---|---|---|---|---|---|
| Linear Alkylbenzene Sulfonate | 21.0 | 21.0 | 12.0 | 13.0 | — |
| Alkyl Ethoxy Sulfate AExS* | — | — | 14.0 | 5.0 | 17.0 |
| w % linear in alkyl chain |  |  | 76 | 84 | 60 |
| w % branching in alkyl chain |  |  | 24 | 16 | 40 |
| C12-14 alpha olefin sulfonate | — | — | — | — | 6.0 |
| Coco amido propyl Amine Oxide | — | — | — | 1.0 | 5.0 |
| alkylpolyglucoside | — | 2.0 | — | — | — |
| Nonionic |  |  |  |  |  |
| C9-11 EO8 (15% branching) | — | — | 8.0 | — | 3.0 |
| Lutensol TO7 (100% branching) | 5.0 | 4.0 | — | 8.0 | — |
| GLDA¹ | 0.5 | — | — | — | — |
| DTPMP² | — | 0.8 | — | — | — |
| DTPA³ | — | — | 0.5 | 0.8 | — |
| MGDA⁴ | — | — | — | — | 1.0 |
| Average branching weight % in total surfactant mixture | 19.2 | 14.8 | 13.4 | 32.6 | 23.4 |
| Total surfactant/Nonionic weight ratio | 5.2 | 4.5 | 4.2 | 3.4 | 10.3 |

|  | Ex. 17 | Ex. 18 | Ex. 19 | Ex. 20 | Ex. 21 |
|---|---|---|---|---|---|
| Alkyl Ethoxy Sulfate AExS* | 17.0 | 12.0 | 24.5 | 18.0 | 29.0 |
| w % linear in alkyl chain | 40 | 76 | 84 | 70 | 70 |
| w % branching in alkyl chain | 60 | 24 | 16 | 30 | 30 |
| C12-14 alpha olefin sulfonate | — | — | 1.0 | — | — |
| Paraffin Sulfonate (C15) | 9.0 | 1.0 | 1.0 | — | — |
| Coco amido propyl amine oxide | — | 6.0 | — | — | 1.0 |
| Coco amido propyl Betaine | — | — | — | 5.0 | — |
| Alkylpolyglucoside | — | 3.0 | — | — | — |
| Nonionic |  |  |  |  |  |
| C9-11 EO8 (15% branching) | 8.0 | — | — | 3.0 | — |
| Lutensol TO7 (100% branching) | — | 2.0 | 2.5 | — | 4.0 |
| GLDA¹ | 0.5 | — | — | — | — |
| DTPMP² | — | 0.8 | — | — | — |
| DTPA³ | — | — | 0.5 | 0.8 | — |
| MGDA⁴ | — | — | — | — | 1.0 |
| Polypropylene glycol MW2000 | 1.0 | 1.0 | — | 0.5 | 0.5 |
| Average branching weight % in total surfactant mixture | 33.5 | 20.3 | 22.1 | 22.5 | 37.4 |

| | | | | | |
|---|---|---|---|---|---|
| Total surfactant/Nonionic weight ratio | 4.2 | 4.8 | 11.6 | 8.7 | 8.5 |
| Balance of Minors (**), Malodor Control Component, and water up to 100% | | | | | |

*Alkyl chain between C10 and C14, alternatively between C12-13 and x = between 0 and 4, alternatively between 0.5 and 2
(**) Minors: dyes, opacifiers, perfumes, preservatives, hydrotropes, processing aids, salts, stabilizers . . .
[1] Glutamic acid
[2] Diethylenetriamine penta methylphosphonic acid
[3] Diethylenetriamine pentaacetic acid
[4] Methyl glycinediacetic acid Analytical Test—Effect of Volatile Aldehydes on Amine-Based and Sulfur-Based Malodors Malodor standards are prepared by pipeting 1 mL of butylamine (amine-based malodor) and butanethiol (sulfur-based malodor) into a 1.2 liter gas sampling bag. The bag is then filled to volume with nitrogen and allowed to sit for at least 12 hours to equilibrate.

A 1 µL sample of each volatile aldehyde listed in Table 6 and of each Accord (A, B, and C) listed in Tables 1 to 3 is pipeted into individual 10 mL silanized headspace vials. The vials are sealed and allowed to equilibrate for at least 12 hours. Repeat 4 times for each sample (2 for butylamine analysis and 2 for butanethiol analysis).

After the equilibration period, 1.5 mL of the target malodor standard is injected into each 10 mL vial. For thiol analysis, the vials containing a sample +malodor standard are held at room temperature for 30 minutes. Then, a 1 mL headspace syringe is then used to inject 250 µL of each sample/malodor into a GC/MS split/splitless inlet. For amine analysis, a 1 mL headspace syringe is used to inject 500 µL of each sample/malodor immediately into the GC/MS split/splitless inlet. A GC pillow is used for the amine analysis to shorten the run times.

Samples are then analyzed using a GC/MS with a DB-5, 20 m, 1 µm film thickness column with an MPS-2 autosampler equipment with static headspace function. Data is analyzed by ion extraction on each total ion current (56 for thiol and 30 for amine) and the area is used to calculate the percent reduction from the malodor standard for each sample.

Table 6 shows the effect of certain volatile aldehydes on neutralizing amine-based and sulfur based malodors at 40 seconds and 30 minutes, respectively.

TABLE 6

| Perfume Raw Material (R—CHO) | At least 20% butylamine reduction at 40 secs.? | At least 20% butanethiol reduction at 30 mins.? |
|---|---|---|
| 2,4,5 Trimethoxy Benzaldehyde | No | No |
| 2,4,6-Trimethoxy-benzylaldehyde | No | No |
| 2-ethoxy benzylaldehyde | Yes | Yes |
| 2-isopropyl-5-methyl-2-hexenal | Yes | Yes |
| 2-methyl-3-(2-furyl)-propenal | No | No |
| 3,4,5 Trimethoxy Benzaldehyde | No | No |
| 3,4-Trimethoxy-benzylaldehyde | No | No |
| 4-tertbutyl benzylaldehyde | Yes | No |
| 5-methyl furfural | Yes | Yes |
| 5-methyl-thiophene-carboxaldehyde | No | Yes |
| Adoxal | Yes | No |
| Amyl cinnamic aldehyde | No | No |
| Benzylaldehyde | Yes | No |
| Bourgenal | No | Yes |
| Cinnamic aldehyde | Yes | Yes |
| Citronelyl Oxyacetaldehyde | No | No |
| Cymal | Yes | No |
| Decyl aldehyde | Yes | No |
| Floral Super | Yes | Yes |
| Florhydral | Yes | Yes |
| Floralozone | No | No |
| Helional | Yes | No |
| Hydroxycitronellal | No | No |
| Lauric aldehyde | Yes | No |
| Ligustral | Yes | No |
| Lyral | Yes | No |
| Melonal | Yes | No |
| Methyl nonyl acetaldehyde | No | No |
| o-anisaldehyde | Yes | Yes |
| p-anisaldehyde | Yes | No |
| Pino acetaldehyde | Yes | Yes |
| P.T. Bucinal | Yes | No |
| Thiophene Carboxaldehyde | Yes | No |
| Trans-4-decenal | Yes | Yes |
| Trans Trans 2,4-Nonadienal | Yes | No |
| Undecyl aldehyde | Yes | No |

Table 7 shows the percent reduction of butylamine and butaniethiol at 40 seconds and 30 minutes, respectively, for Accords A, B, and C.

TABLE 7

| Accord | % reduction of butylamine at 40 secs. | % reduction of butanethiol at 30 mins. |
|---|---|---|
| Accord A | 76.58 | 25.22 |
| Accord B | 51.54 | 35.38 |
| Accord C | 65.34 | 24.98 |

Analytical Test—Effect of Acid Catalysts on Sulfur-Based Malodors

The above analytical test is repeated using samples containing an acid catalyst to test their effect on sulfur-based malodors. Specifically, a 1 µL aliquot of each of the following controls and acid catalyst samples are pipeted into individual 10 mL silanized headspace vials in duplicate: thiophene carboxyaldehyde as a control; a 50/50 mixture of thiophene carboxaldehyde and each of the following acid catalysts at 0.04%, 0.10%, 0.43% in DPM, 1.02% in DPM, and 2.04% in DPM: phenol, mesitylenic acid, caprylic acid, succinic acid, pivalic acid, tiglic acid, and benzoic acid.

FIG. 1 demonstrates that low vapor pressure acid catalysts provide up to 3 times better reduction of sulfur-based malodors in comparison to the control.

Analytical Test—Effect of Volatile Aldehydes and Acid Catalyst on Amine-Based and Sulfur-Based Malodors The above analytical test is repeated using sample formulations containing volatile aldehydes (or RA) and an acid catalyst, as outlined in Tables 8 and 9.

Tables 8 and 9 show that a perfume mixture having as little as 1% volatile aldehyde along with 1.5% acid catalyst performs better at reducing butylamine and butanethiol than the same perfume mixture having 5% volatile aldehyde.

TABLE 8

| Formulation | % butylamine reduction at 40 secs. | | % butanethiol reduction at 30 mins. | |
|---|---|---|---|---|
| Perfume Mixture w/5% RA (Control) | 34.21 | — | 2.40 | — |
| Perfume Mixture w/1% RA and w/1.5% Benzoic Acid | 41.63 | +7.42 | 11.95 | +9.55 |
| Perfume Mixture w/3% RA and w/1.5% Benzoic Acid | 36.19 | +1.98 | 13.56 | +11.16 |
| Perfume A Mixture w/5% RA and w/1.5% Benzoic Acid | 41.26 | +7.05 | 9.56 | +5.02 |

TABLE 9

| Formulation | % butylamine Reduction at 40 secs. | | % butanethiol reduction at 30 mins. | |
|---|---|---|---|---|
| Perfume mixture w/5% RA (Control) | 4.94 | — | 10.52 | — |
| Perfume mixture w/1% RA and w/1.5% Benzoic Acid | 11.61 | +6.67 | 18.82 | +8.30 |
| Perfume mixture w/3% RA and w/1.5% Benzoic Acid | 26.89 | +21.95 | 14.85 | +4.33 |
| Perfume mixture w/5% RA and w/1.5% Benzoic Acid | 20.27 | +15.33 | 16.84 | +6.32 |

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests, or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is, therefore, intended to cover in the appended claims all such changes and modifications that are within the scope of this invention.

What is claimed:

1. A dishwashing detergent composition comprising:
   (a) a chelant;
   (b) a surfactant selected from the group consisting of anionic, nonionic, cationic, amphoteric, zwitterionic, semi-polar nonionic surfactants, and mixtures thereof; and
   (c) a malodor control component comprising:
      (i) at least one volatile aldehyde; and
      (ii) 5 methyl thiophene carboxylic acid; and
   (b) about 1% to about 5%, by weight of said composition, of a low molecular weight monohydric alcohol.

2. The composition of claim 1 wherein said at least one volatile aldehyde has a VP of about 0.001 to about 50 torr.

3. The composition of claim 1 wherein said at least one volatile aldehyde has a VP of about 0.001 ton to about 15 ton.

4. The composition of claim 1 wherein said at least one volatile aldehyde is selected from the group consisting of 2-ethoxy benzylaldehyde, 2-isopropyl-5-methyl-2-hexenal, 5-methyl furfural, 5-methyl-thiophene-carboxaldehyde, adoxal, p-anisaldehyde, benzylaldehyde, bourgenal, cinnamic aldehyde, cymal, decyl aldehyde, floral super, florhydral, helional, lauric aldehyde, ligustral, lyral, melonal, o-anisaldehyde, pino acetaldehyde, P.T. bucinal, thiophene carboxaldehyde, trans-4-decenal, trans trans 2,4-nonadienal, undecyl aldehyde, and mixtures thereof.

5. The composition of claim 1 wherein said at least one volatile aldehyde is selected from the group consisting of flor super, o-anisaldehyde, and mixtures thereof.

6. The composition of claim 1 wherein said at least one volatile aldehyde is present in an amount from about 1% to about 10%, by weight of said malodor control component.

7. The composition of claim 1 wherein said at least one volatile aldehyde is present in an amount from about 0.015% to about 1%, by weight of said dishwashing detergent composition.

8. The composition of claim 1 wherein said at least one volatile aldehyde is present in an amount from about 1% to about 5%, by weight of said malodor control component, and 5-methyl thiophene carboxylic acid is present in an amount of about 0.4% to about 1.5%, by weight of said malodor control component.

9. The composition of claim 1 wherein 5-methyl thiophene carboxylic acid is present in an amount from about 0.1% to about 0.4%, by weight of said malodor control composition.

10. A method of cleaning a dishware comprising the steps of:
   (a) applying a composition according to claim 1 on said dishware; and
   (b) rinsing said composition off of said dishware.

* * * * *

UNITED STATES PATENT AND TRADEMARK OFFICE
CERTIFICATE OF CORRECTION

PATENT NO. : 8,461,089 B2
APPLICATION NO. : 12/969639
DATED : June 11, 2013
INVENTOR(S) : Woo et al.

Page 1 of 1

It is certified that error appears in the above-identified patent and that said Letters Patent is hereby corrected as shown below:

In the Claims, Col. 26, Claim 3
Line 16, delete "0.001 ton to about 15 ton." and insert -- 0.001 torr to about 15 torr. --

Signed and Sealed this
Twenty-third Day of July, 2013

Teresa Stanek Rea
*Acting Director of the United States Patent and Trademark Office*